United States Patent [19]

Castenson et al.

[11] 4,033,986
[45] July 5, 1977

[54] PROCESS FOR THE PREPARATION OF 4-BROMO-1,8-NAPHTHALIC ACID ANHYDRIDE

[75] Inventors: Richard L. Castenson, Coventry; James R. Hazen; Rex Y. Tien, both of Warwick, all of R.I.

[73] Assignee: American Hoechst Corporation, Bridgewater, N.J.

[22] Filed: Feb. 11, 1976

[21] Appl. No.: 657,304

[52] U.S. Cl. .......................................... 260/345.2
[51] Int. Cl.$^2$ .................................... C07D 311/02
[58] Field of Search ..................... 260/345.2, 548

[56] References Cited
UNITED STATES PATENTS

| | | | |
|---|---|---|---|
| 3,646,069 | 2/1972 | Okada et al. | 260/345.2 |
| 3,850,965 | 11/1974 | Williams | 260/345.2 |
| 3,888,885 | 6/1975 | Dencker et al. | 260/345.2 |

OTHER PUBLICATIONS

Farkas et al., "J.A.C.S.", vol. 71, 1988 (1949).

*Primary Examiner*—Norman Morgenstern
*Attorney, Agent, or Firm*—Curtis, Morris & Safford

[57] ABSTRACT

A novel method for the preparation of 4-bromo-1,8-naphthalic acid anhydride is disclosed. This method is carried out by the bromination, with alkali metal bromide or molecular bromine in the presence of a hypohalite, of a di-alkali metal salt of 1,8-naphthalic acid in aqueous solution at a pH of between 6.5 and 9.5 and at a temperature of between 0° and 30° C. to a di-alkali metal salt of 4-bromo-1,8-naphthalic acid and cyclizing to produce 4-bromo-1,8-naphthalic acid anhydride. This novel direct bromination method produces the desired product in good yields and high purity. 4-Bromo-1,8-naphthalic acid anhydride is a valuable intermediate for the preparation of dyestuffs, pigments and optical brighteners.

8 Claims, No Drawings

PROCESS FOR THE PREPARATION OF 4-BROMO-1,8-NAPHTHALIC ACID ANHYDRIDE

This invention relates to a novel method for the preparation of 4-bromo-1,8-naphthalic acid anhydride, which is a valuable intermediate for the preparation of dyestuffs, pigments and optical brighteners by direct bromination of a di-alkali metal salt of 1,8-naphthalic acid and cyclization thereof.

Most known direct methods of brominating 1,8-naphthalic acid anhydride lead to the bromination in the 3-rather than the 4-position of the naphthalene ring. One direct bromination method, described by Rule et al., J. Chem. Soc., 1764—1767 (1937), does produce the desired 4-bromo-1,8-naphthalic acid anhydride but in poor yield and insufficient purity, thus requiring an additional purification step. In this method 1,8-naphthalic acid anhydride is directly brominated with molecular bromine under alkaline conditions. The non-direct methods require the use of acenaphthene or derivatives thereof as a starting material. In one such method, described by Okada et al., German Offen. No. 1,930,842 (1970) acenaphthene is brominated and then oxidized in an additional step to the desired 4-bromo-1,8-naphthalic acid anhydride. Such indirect methods not only suffer the disadvantage of requiring an additional reaction step but also require the use of organic solvents and expensive oxidizing reagents. Another known method, Senshu, French Pat. No. 1,405,776 (1965), suggests utilizing acenaphthene as a starting material and requires sulfonating and then oxidizing to 4-sulfonate-1,8-naphthalic acid anhydride. The sulfonic group is replaced by bromine by treatment with phosphorus pentabromide or hydrobromic acid and sodium bromate. This procedure also suffers from the disadvantage of being a multi-step process. U.S. Pat. No. 3,888,885 to Deucker and Troster describes a process for preparing 4-chloronaphthalic acid anhydride by chlorinating naphthalic acid anhydride, the chlorinating agent being chlorine gas in the presence of alkali or sodium hypochlorite solution.

In accordance with the present invention, 4-bromonaphthalic anhydride is prepared from readily available naphthalic acid anhydride in good yield and quality by dissolving naphthalic acid anhydride in aqueous alkali metal hydroxide solution to form the corresponding di-alkali metal salt of 1,8-naphthalic acid and treating the resultant solution with an alkali metal bromide or molecular bromine and a hypochlorite under conditions of controlled pH and temperature.

According to one embodiment of the invention, sufficient alkali metal bromide and sodium or potassium hypochlorite are introduced into an aqueous solution of the di-sodium salt or, preferably, the di-potassium, salt of 1,8-naphthalic acid at a pH of 6.5 to 9.5, preferably at a pH of 7.2 to 7.8 to brominate the starting material substantially completely. Any combination of sodium bromide or potassium bromide and sodium hypochlorite or potassium hypochlorite will work equally well. When sodium hypochlorite and sodium bromide are use, 1.50 moles of sodium hypochlorite and 1.25 moles of sodium bromide are required per mole of naphthalic acid anhyride. The pH is controlled in the desired range during the reaction by the simultaneous addition of a suitable acid, for example, hydrochloric acid. After addition of the alkali metal hypohalite, or other oxidizing agent, such as calcium hypochlorite, or chlorine and alkali, suitable for generating the effective brominating agent and capable of functioning in the pH range of 6.5 to 9.5, the mixture is stirred at constant pH until all of the hypohalite is consumed as shown by a negative test with potassium iodide starch paper.

According to another embodiment of the invention, molecular bromine is introduced into an aqueous solution of the di-sodium salt or, preferably, the di-potassium salt, of naphthalic acid at pH 6.5 to 9.5, 0.6 to 0.7 mole of bromine per mole of naphthalic anhydride being required. When the starting material is the di-sodium salt of 1,8-naphthalic acid, the preferred pH range for the bromine addition, in order to maximize product quality, is 7.2 to 7.8, maintained in this range by the simultaneous addition of a sodium hydroxide solution. When the starting material is the di-potassium salt of naphthalic acid, the preferred pH range for the reaction if 8.5 to 9.0, in order to maximize product quality, maintained by the simultaneous addition of a potassium hydroxide solution. In either event, when the bromine addition is complete, the mixture is stirred briefly and then treated with aqueous hypochlorite solution to complete the bromination. The same preferred pH ranges as in the bromine addition step, i.e. 7.2–7.8 or 8.5–9.0 for the disodium and di-potassium salts, respectively, of 1,8-naphthalic acid, are maintained during the hypochlorite addition by the simultaneous addition of a suitable acid, for example, hydrochloric acid or phosphoric acid. When the bromination is conducted in the preferred pH ranges, 1.2 to 1.4 moles of bromine, calculated as hypobromite, are required per mole of naphthalic anhydride to achieve the desired degree of bromination. By this method maximum utilization of the total amount of bromine is achieved in the conversion to 4-bromonaphthalic anhydride and the quantity of corrosive liquid bromine that is required is reduced to a minimum.

According to both embodiments of this invention, the bromination is conducted at temperatures ranging from about 0° to 30° C, preferably 20° to 25° C. Lower temperatures cause the reaction to proceed too slowly and higher temperatures for all but the briefest times result in excessive formation of oxidative side products and destruction of the brominating agent.

The concentration range of the hypohalite in the reaction mixture is not critical and the concentration is generally low since the reaction proceeds rapidly. The use of other oxidizing agents such as calcium hypochlorite or chlorine gas and alkali, is also permissable. In the embodiment wherein alkali metal bromide, chlorine gas and alkali are used, and without being bound by theory, it is believed that the chlorine gas either directly oxidizes the bromide ion to the effective brominating agent or first reacts with the alkali to form hypochlorite which then oxidizes the bromide ion to the brominating agent. The oxidation proceeds rapidly and with the virtual exclusion of any chlorination of the di-alkali metal salt of 1,8-naphthalic acid. It is surprising that in both embodiments of this invention, the brominated product is prepared with only a trace of the chloro analog, even though in the absence of bromide ion, hypochlorite will react with 1,8-naphthalic acid anhydride to form 4-chloronaphthalic acid anhydride. Only trace amounts of 4-chloronaphthalic anhydride are found in the 4-bromonaphthalic anhydride prepared according to the processes of the present invention.

The starting material for both processes of this invention for the preparation of 4-bromo-1,8-naphthalic acid anhydride is 1,8-naphthalic acid anhydride, which is dissolved in hot water with sodium hydroxide or, preferably, potassium hydroxide and thereby hydrolyzes to the corresponding dialkali metal salt. Potassium hydroxide is preferred because of the greater water solubility of the di-potassium salt of naphthalic acid than that of the di-sodium salt. To accelerate the solution step, it is preferable to use excess sodium or potassium hydroxide. Then, when solution is complete, the pH is adjusted to the desired value prior to bromination by the addition of the appropriate amount of a suitable acid such as hydrochloric acid, sulfuric acid, acetic acid or phosphoric acid. Phosphoric acid is the preferred reagent because its superior buffering capabilities in the pH range of interest most readily allows satisfactory control of the pH of the reaction mixtures.

After the bromination is complete, the reaction mixture is worked up according to known techniques. After optionally clarifying the mixture by filtration with or without activated carbon, the mixture is treated with sodium bisulfite to insure the destruction of any residual hypohalite, and finally acidified with mineral acid to pH 1 to 2 and heated at a temperature up to 90° C to reform the anhydride ring and precipitate the product. The 4-bromonaphthalic anhydride is isolated by filtration of the reaction mixture, preferably while hot and preferably after the pH has been adjusted to 4.5 with dilute aqueous alkali. An especially pure product is obtained when the 4-bromo-1,8-naphthalic acid anhydride, prepared as described, is reconverted to its disodium or perferably its dipotassium salt, the aqueous solution of which is salted out by the addition, for example, of sodium chloride. The precipitated 4-bromo-1,8-naphthalic dicarboxylic acid salt, predominantly as the di-sodium salt, is separated and then reconverted into the purified anhydride by treatment with aqueous mineral acid.

According to the conditions chosen within the scope of the processes described in this invention, 4-bromo-1,8-naphthalic acid anhydride is obtained in yields of 77 to 85% of the theoretical amount and having any assay of 87 to 98% of pure material and containing 0 to 2% of unconverted naphthalic anhydride.

The 4-bromo-1,8-naphthalic acid anhydride is a valuable intermediate for the production of dyestuffs, pigments and optical brighteners.

The following examples illustrate the invention:

EXAMPLE 1

100 g of 1,8-naphthalic acid anhydride are dissolved in a solution of 1200 ml water, 73.8 g potassium hydroxide (85% flakes) and 65 g sodium bromide. While the temperature of the solution is maintained at 20°–25° C, the pH is adjusted to 7.5 with 85% phosphoric acid. 496 g of sodium hypochlorite solution of 13% are then added while the pH is maintained at 7.2–7.8 by the simultaneous addition of hydrochloric acid. When there is no longer any hypohalite present, the pH is lowered to 1.5 with hydrochloric acid and the mixture is heated to 70°–80° C for 1.5 hours. The pH of the mixture is then raised to 4.5 with dilute sodium hydroxide solution and the mixture is then suction-filtered, washed with water, and dried. The yield is 108 g of material that has a 90–92% assay of pure 4-bromo-1,8-naphthalic acid anhydride.

EXAMPLE 2

100 g of 1,8-naphthalic acid anhydride are dissolved in a solution of 2400 ml water, 100 g of 50% aqueous solution of sodium hydroxide and 65 g of sodium bromide. The bromination, cyclization, and isolation are done in the manner described in Example 1 to yield 108 g of material that has a 90–92% assay of 4-bromo-1,8-naphthalic acid anhydride.

EXAMPLE 3

100 g of 1,8-naphthalic acid anhydride are dissolved at 55° C in 1200 ml of water containing 100 g of a 50% sodium hydroxide solution. At 15°–20° C the pH is adjusted to 7.2 to 7.8 with phosphoric acid and 50 g of bromine are added so that 200 g of 25% sodium hydroxide solution are consumed to maintain the pH in the range of 7.2 to 7.8. When the bromine addition is complete, a 10–12% sodium hypochlorite solution is added to the mixture while the pH is maintained at 7.2 to 7.8 with phosphoric acid. The reaction mixture is then acidified with hydrochloric acid and heated at 80° C. The precipitate is filtered, washed with water and dried at 100° C to 120° C. The yield is 104 g to 112 g, the content of pure 4-bromo-1,8-naphthalic acid anhydride being 90–92%.

EXAMPLE 4

100 g of 1,8-naphthalic acid anhydride are dissolved as in Example 3 with, instead of sodium hydroxide, the equivalent amount of potassium hydroxide solution. The pH of the solution is adjusted to 8.5 to 9.0 with phosphoric acid and 50 g of bromine are added along with the simultaneous addition of 45 g of 50% potassium hydroxide solution to maintain the pH at 8.5 to 9.0. When the addition is complete, a 10–12% solution of sodium hypochlorite is added dropwise while maintaining the pH at 8.5–9.0 with the addition of phosphoric acid. The mixture is acidified with hydrochloric acid and heated at 80° C. The pH is adjusted to pH 4.0 and the precipitated product is collected as described in Example 3. The yield is 99 g, the content of pure 4-bromo-1,8-naphthalic acid anhydride being 90–92%.

EXAMPLE 5

100 grams of 1,8-naphthalic acid anhydride are dissolved in a solution of 1200 ml water, 73.8 grams potassium hydroxide (85% flakes) and 75 grams potassium bromide. While the temperature of the solution is maintained at 20°–25° C, th pH is adjusted to 7.5 with 85% phosphoric acid. 600 grams of potassium hypochlorite solution of 13% are then added while the pH is maintained at 7.2–7.8 by the simultaneous addition of hydrochloric acid. When there is no longer any hypohalite present, the pH is lowered to 1.5 with hydrochloric acid and the mixture is heated to 70°–80° C for 1.5 hours. The pH of the mixture is then raised to 4.5 with dilute sodium hydroxide solution and the mixture is then suction-filtered, washed with water, and dried. The yield is 108 grams of material that has a 90–92% assay of pure 4-bromo-1,8-naphthalic acid anhydride.

We claim:

1. A process for the preparation of 4-bromo-1,8-naphthalic acid anhydride which comprises brominating a di-alkali metal salt of 1,8-naphthalic acid in an aqueous solution at a pH between 6.5 and 9.5 to the di-alkali metal salt of 4-bromo-1,8-naphthalic acid with a brominating agent comprising 1. an alkali metal bromide, or
2. molecular bromine, in the presence of either a. a hypochlorite, or
b. chlorine gas and alkali, at a temperature between 0° and 30° C.

2. The process as defined in claim 1 wherein the temperature is between 20° and 25° C.

3. The process as defined in claim 1 wherein the di-alkali metal salt is the potassium salt.

4. The process as defined in claim 1 wherein the pH is between 7.2 and 7.8 and the brominating agent is sodium or potassium bromide and sodium or potassium hypochlorite.

5. The process as defined in claim 1 wherein the di-alkali metal salt of 1,8-naphthalic acid is the di-sodium salt, the pH is between 7.2 and 7.8 and the brominating is carried out by successive addition of molecular bromine and sodium hypochlorite.

6. The process as defined in claim 1 wherein the di-alkali metal salt of 1,8-naphthalic acid is the di-potassium salt, the pH is between 8.5 and 9.0 and the brominating is carried out by successive addition of molecular bromine and sodium or potassium hypochlorite.

7. The process as defined in claim 1 wherein the brominating is carried out in the presence of calcium hypochlorite.

8. The process as defined in claim 1 wherein the brominating is carried out in the presence of chlorine and alkali.

* * * * *